(12) United States Patent
Carpentier et al.

(10) Patent No.: US 11,872,413 B2
(45) Date of Patent: Jan. 16, 2024

(54) CONTROL METHOD FOR THE TREATMENT OF BRAIN TISSUE USING AN ULTRASONIC PROBE AND AN IMPLANTED ACOUSTIC WINDOW ON THE CRANIUM

(71) Applicants: ASSISTANCE PUBLIQUE HOPITAUX DE PARIS, Paris (FR); SORBONNE UNIVERSITE, Paris (FR); CARTHERA, Paris (FR)

(72) Inventors: Alexandre Carpentier, Paris (FR); Guillaume Bouchoux, Lyons (FR); Michael Canney, Denver, CO (US); Francois Lacoste, Paris (FR)

(73) Assignees: ASSISTANCE PUBLIQUE HOPITAUX DE PARIS, Paris (FR); SORBONNE UNIVERSITE, Paris (FR); CARTHERA, Paris (FR)

( * ) Notice: Subject to any disclaimer, the term of this patent is extended or adjusted under 35 U.S.C. 154(b) by 385 days.

(21) Appl. No.: 16/623,964

(22) PCT Filed: Jun. 19, 2018

(86) PCT No.: PCT/EP2018/066205
§ 371 (c)(1),
(2) Date: Dec. 18, 2019

(87) PCT Pub. No.: WO2018/234282
PCT Pub. Date: Dec. 27, 2018

(65) Prior Publication Data
US 2020/0139159 A1 May 7, 2020

(30) Foreign Application Priority Data
Jun. 19, 2017 (FR) ...................................... 1755565

(51) Int. Cl.
*A61N 7/00* (2006.01)

(52) U.S. Cl.
CPC ........ *A61N 7/00* (2013.01); *A61N 2007/0021* (2013.01); *A61N 2007/0078* (2013.01)

(58) Field of Classification Search
CPC .............. A61N 7/00; A61N 2007/0021; A61N 2007/0078; A61N 2007/0004;
(Continued)

(56) References Cited

U.S. PATENT DOCUMENTS

| 4,348,289 A | 9/1982 | Snavely et al. |
| 4,530,358 A | 7/1985 | Forssmann et al. |

(Continued)

FOREIGN PATENT DOCUMENTS

| EP | 2539021 B1 | 2/2016 |
| EP | 3020450 A1 | 5/2016 |

(Continued)

OTHER PUBLICATIONS

Bing et al., "Blood-Brain Barrier (BBB) Disruption Using a Diagnostic Ultrasound Scanner and Definity® in Mice", Ultrasound Med. Biol., vol. 35, No. 8, pp. 1298-1308, 2009.
(Continued)

*Primary Examiner* — Serkan Akar
*Assistant Examiner* — Neshat Baset
(74) *Attorney, Agent, or Firm* — BCF LLP

(57) ABSTRACT

The present invention relates to a method for controlling a probe for the treatment of brain tissue using an assembly comprising the probe and an acoustic window (1), the probe (2) including a plurality of transducers (21) for generating ultrasound waves, the method comprising: —a phase of detection: •of the probe transducers situated above the cranium (4) of the patient, and •of the probe transducers situated above the acoustic window (1), so as to permit: •deactivation of the transducers situated above the cranium
(Continued)

(4) of the patient, •activation of the transducers situated above the acoustic window (1).

19 Claims, 4 Drawing Sheets

(58) Field of Classification Search
CPC .... A61N 2007/0043; A61N 2007/0056; A61N 2007/006
See application file for complete search history.

(56) References Cited

U.S. PATENT DOCUMENTS

| | | | |
|---|---|---|---|
| 5,246,595 A | | 9/1993 | Bourlion et al. |
| 6,635,017 B1* | | 10/2003 | Moehring ........ A61B 17/22004 |
| | | | 600/459 |
| 9,044,195 B2 | | 6/2015 | Manwaring et al. |
| 9,095,695 B2* | | 8/2015 | Fedewa .................. A61B 34/10 |
| 2005/0165312 A1 | | 7/2005 | Knowles et al. |
| 2009/0227830 A1 | | 9/2009 | Pillutla et al. |
| 2010/0143241 A1 | | 6/2010 | Johnson et al. |
| 2010/0179425 A1* | | 7/2010 | Zadicario ................. A61N 7/02 |
| | | | 600/438 |
| 2010/0217160 A1 | | 8/2010 | Saguchi et al. |
| 2012/0209150 A1 | | 8/2012 | Zeng et al. |
| 2013/0158578 A1* | | 6/2013 | Ghodke ......... A61B 17/320783 |
| | | | 606/170 |
| 2013/0289411 A1 | | 10/2013 | Barnard et al. |
| 2014/0330123 A1* | | 11/2014 | Manwaring .......... A61B 8/0808 |
| | | | 600/443 |
| 2015/0321026 A1 | | 11/2015 | Branson et al. |
| 2016/0184026 A1* | | 6/2016 | Tlusty .................... A61B 6/501 |
| | | | 600/407 |
| 2016/0296769 A1* | | 10/2016 | Barthe ..................... A61N 7/02 |
| 2018/0071553 A1* | | 3/2018 | Vortman .................. A61N 7/00 |

FOREIGN PATENT DOCUMENTS

| | | |
|---|---|---|
| WO | 89/07907 A1 | 9/1989 |
| WO | 93/14712 A1 | 8/1993 |
| WO | 2007/064453 A2 | 6/2007 |
| WO | 2014179720 A1 | 11/2014 |
| WO | 2016202955 A1 | 12/2016 |

OTHER PUBLICATIONS

Carpentier et al., "Clinical trial of blood-brain barrier disruption by pulsed ultrasound", Science TranslationalMedicine, vol. 8, No. 343, 2016.

Eames et al., "Trans-cranial focused ultrasound without hair shaving: feasibility study in an ex vivo cadaver model", Journal of Therapeutic ultrasound, vol. 1, No. 24, 2013.

Guess et al., "Acoustic properties of some biocompatible polymers at body temperature", Ultrasound Med. & Biol., vol. 21, No. 2, pp. 273-277, 1995.

Hynynen et al., "Noninvasive MR Imaging-guided Focal Opening of the Blood-Brain Barrier in Rabbits", Radiology, vol. 220, N. 3, pp. 640-646, 2001.

Marquet et al., "Noninvasive, Transient and Selective Blood-Brain Barrier Opening in Non-Human Primates In Vivo", PLoS One, vol. 6, No. 7, 2011.

McDannold et al., "Temporary Disruption of the Blood-Brain Barrier by Use of Ultrasound and Microbubbles: Safety and Efficacy Evaluation in Rhesus Macaques", Cancer Res., vol. 72, No. 14, pp. 3652-3663, 2012.

Melamed et al., "Sonographic Appearance of Oxidized Cellulose (Surgicel): Pitfall in the Diagnosis of Postoperative Abscess", J. Ultrasound Med., vol. 14, No. 1, pp. 27-30, Jan. 1995.

Raymond et al., "Acoustic Transmission Losses and Field Alterations Due to Human Scalp Hair", IEEE Transactions on Ultrasonics, Ferroelectrics, and Frequency Control, vol. 52, No. 8, pp. 1415-1419, Aug. 2005.

Sparing et al., "Transcranial Magnetic Stimulation and the Challenge of Coil Placement: A Comparison of Conventional and Stereotaxic Neuronavigational Strategies", Human Brain Mapping, vol. 29, No. 1, pp. 82-96, Jan. 2008.

Tobias et al., "An ultrasound window to perform scanned, focused ultrasound hyperthermia treatments of brain tumors", Medical Physics, vol. 14, No. 2. pp. 228-234, 1987.

Van der Bom et al., "Frameless multimodal image guidance of localized convection-enhanced delivery of therapeutics in the brain", J. Neurointerv. Surg., vol. 5, No. 1, pp. 69-72, Jan. 2013.

Wei et al., "Neuronavigation-Guided Focused Ultrasound-Induced Clood-Brain Barrier Opening: A Preliminary Study in Swine", AJNR. Am. J. Neuroradiol., vol. 34, No. 1, pp. 115-120, Jan. 2013.

* cited by examiner

CONTROL METHOD FOR THE TREATMENT OF BRAIN TISSUE USING AN ULTRASONIC PROBE AND AN IMPLANTED ACOUSTIC WINDOW ON THE CRANIUM

CROSS-REFERENCE TO RELATED APPLICATIONS

This application is a national phase filing under 35 U.S.C. § 371 of International Application No. PCT/EP2018/066205 filed on Jun. 19, 2018, which claims benefit of priority from French Patent Application No. 1755565 filed Jun. 19, 2017, the contents of which are hereby incorporated by reference in their entirety.

FIELD OF THE INVENTION

The present invention relates to the general technical field of control methods for treating a human or animal brain tissue by ultrasounds in order to assist a practitioner in treating a pathology.

BACKGROUND OF THE INVENTION

Various techniques for treating a brain tissue are known. In particular, one known technique consists in using an assembly composed of:
an acoustic window made of an acoustically transparent material, and
an ultrasonic probe able to generate ultrasonic waves.

The acoustic window is implanted at an opening arranged in the cranium of a patient. This window allows facilitating the transmission of the ultrasonic waves (generated by the probe) through the cranium of the patient. Indeed, the bones of the cranium tend to disturb the transmission of the ultrasonic waves.

The operating principle of such an assembly in the case of the treatment of a brain tissue of interest is as follows.

Once the acoustic window implanted into the skull of the patient, a succession of treatment sessions are provided to the latter to treat a pathology affecting him.

At each new treatment session, the probe is positioned above the acoustic window and then activated to emit ultrasonic waves towards the brain tissue of interest to be treated.

A disadvantage of such an assembly is that it is difficult for the practitioner to accurately position the probe in line with the acoustic window. Indeed, once implanted, the window is covered with the skin of the skull, so that its accurate position is not known.

If the ultrasonic probe is not accurately positioned in line with the transparent window, ultrasonic waves can be emitted toward the patient's bone. This may:
cause burns at the skull of the patient, and/or
limit the therapeutic action of the ultrasonic waves, the brain tissue not receiving a sufficient dose of ultrasonic waves to ensure good effectiveness of the treatment.

An object of the present invention is to propose a method for controlling a probe for the treatment of a brain tissue from an assembly composed of an acoustic window and of the ultrasonic probe, and making it possible to overcome at least one of the aforementioned disadvantages.

In particular, an object of the invention is to propose a method for controlling a probe for the treatment of a brain tissue from an assembly composed of an acoustic window and of the ultrasonic probe making it possible to:
limit the risks of burning of a patient and/or
improve the effectiveness of the ultrasonic wave treatment.

SUMMARY

For this purpose, the invention proposes a method for controlling a probe for the treatment of a brain tissue from an assembly comprising the probe and an acoustic window intended to be implanted at an opening arranged into the cranium of a patient, the probe including a plurality of ultrasonic wave generation transducers, and being intended to be positioned in line with the acoustic window, remarkable in that the method comprises:
a detection phase:
transducers of the probe situated above the cranium of the patient, and
transducers of the probe situated above the acoustic window,
to enable:
the deactivation of the transducers of the probe situated above the cranium of the patient,
the activation of the transducers of the probe situated above the acoustic window, said transducers being able to generate ultrasonic treatment waves in order to treat the brain tissue.

Preferred but non-limiting aspects of the present invention are the following:
the detection phase may further comprise a step of refocusing the probe above the acoustic window,
the refocusing step may comprise a sub-step of comparing the position of the barycentre of the probe transducers with the position of the barycentre of the probe transducers situated above the acoustic window,
the detection phase may further comprise a step of orienting the probe depending on the depth of the brain tissue to be treated,
the detection phase may further comprise a step of calculating treatment parameters used during a brain tissue treatment phase,
the treatment parameters may comprise the intensity and duration of emission of the ultrasonic waves to be generated by the transducers situated above the acoustic window,
the step of calculating treatment parameters may comprise at least one of the following sub-steps taken alone or in combination:
calculating at least one treatment parameter as a function of the number of transducers situated above the acoustic window,
calculating at least one treatment parameter as a function of an attenuation or reflection coefficient associated with the acoustic window or with the tissues situated between the probe and the window, and/or of an attenuation coefficient associated with the material constituting a brain tissue traversed by the ultrasonic waves,
the detection phase may comprise the steps of:
emitting, for each transducer, an ultrasonic measurement wave toward the patient's skull from the probe,
measuring, for each transducer, an ultrasonic echo wave reflected from the probe,
processing each ultrasonic echo wave to detect whether the associated transducer is situated above the acoustic window or above the cranium,
processing each ultrasonic wave to estimate an acoustic coupling quality between the probe and the target tissue, the step of processing each ultrasonic echo wave may comprise the comparison of the ultrasonic echo wave with reference signals, and the detection of a variation in an intensity of the ultrasonic echo wave and/or a variation in its appearance time. This step may also include a step of listening to the cavitation, in order to monitor the effect of the ultrasounds on the tissues, thanks to acoustic sensors disposed in the probe and connected to electronics.

the detection phase may comprise a step of calculating the number of transducers situated above the acoustic window, the detection phase may further comprise the steps of:
 comparing the calculated number of transducers situated above the acoustic window with a threshold value,
 if the number of transducers situated above the acoustic window is greater than the threshold value, sending first information to the practitioner, the first information consisting in asking him to immobilize the probe,
 if the number of transducers situated above the acoustic window is smaller the threshold value, sending second information to the practitioner, the second information consisting in asking him to displace the probe on the skull of the patient, the detection phase may comprise a step of emitting displacement information, said displacement information indicating to the practitioner a direction of displacement of the probe, The invention also relates to a computer program product comprising programming code instructions intended to perform the steps of the method described above when said program is run on a computer.

The invention also relates to a device for treating a brain tissue from an assembly comprising an acoustic window intended to be implanted at an opening arranged in the cranium of a patient, and a probe including a plurality of ultrasonic wave generation transducers, the probe being intended to be positioned in line with the acoustic window, remarkable in that the device comprises means for implementing the method described above. Particularly, the device comprises means for:
 detecting the transducers of the probe situated above the cranium of the patient, and
 detecting the transducers of the probe situated above the acoustic window,
 deactivating the transducers of the probe situated above the cranium of the patient,
 activating the transducers of the probe situated above the acoustic window, said transducers being able to generate ultrasonic treatment waves in order to treat the brain tissue.

In particular, the device comprises means for:
 controlling, at each transducer, the emission of an ultrasonic measurement wave toward the skull of the patient,
 controlling, at each transducer, the measurement of a reflected ultrasonic echo wave,
 processing each ultrasonic echo wave to detect whether the associated transducer is situated above the acoustic window or above the cranium,
 processing each ultrasonic wave to estimate an acoustic coupling quality between the probe and the target tissue.

The invention also relates to a method for controlling a probe for the treatment of a brain tissue from an assembly comprising the probe and an acoustic window intended to be implanted at an opening arranged in the cranium of a patient, the probe including a plurality of ultrasonic wave generation transducers and being intended to be positioned in line with the acoustic window, remarkable in that the method comprises a detection phase including the following steps:
 detecting the transducers of the probe situated above the cranium of the patient,
 switching the transducers situated above the cranium in a first state called "deactivated" state in which said transducers do not generate ultrasonic waves in response to an input signal,
 detecting the transducers of the probe situated above the acoustic window,
 switching the transducers situated above the acoustic window (1) in a second state called "activated" state in which said transducers are able to generate ultrasonic waves in response to an input signal.

BRIEF DESCRIPTION OF THE DRAWINGS

Other advantages and characteristics of the method for controlling a probe for the treatment of a brain tissue will become more apparent from the following description of several variants, given by way of non-limiting examples, from the appended drawings in which.

DETAILED DESCRIPTION OF THE INVENTION

Figure 1:
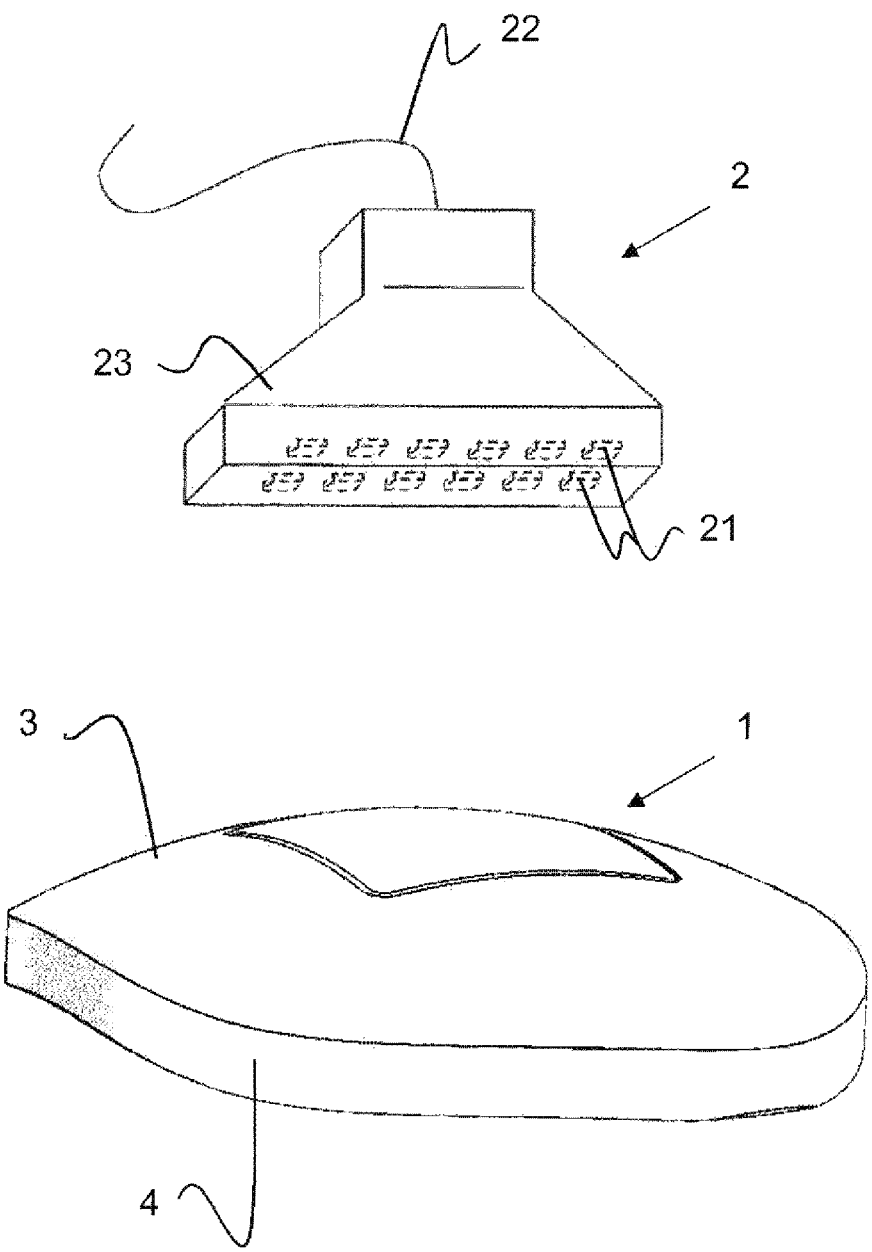
FIG. 1 schematically illustrates an ultrasound treatment assembly comprising an acoustic window and an ultrasonic probe, FIG. 2 schematically illustrates the steps of a method for controlling a probe for the treatment of a pathology from the ultrasound treatment assembly, FIGS. 3A to 3D schematically illustrate, in top view, different positions of the ultrasonic probe relative to the acoustic window.
Figure 2:
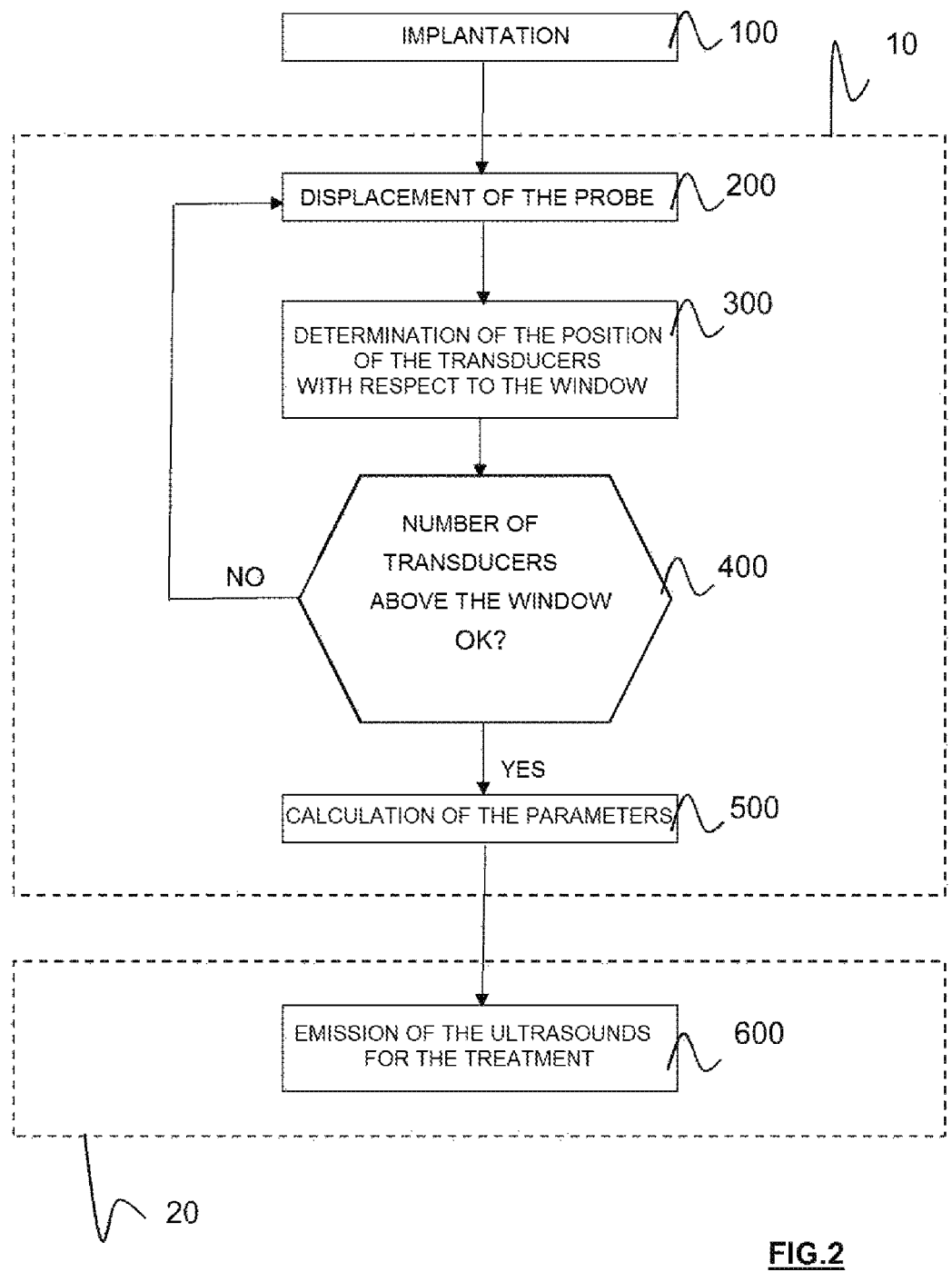

An example of a method for controlling a probe for the treatment of brain tissue from a treatment assembly (composed of an acoustic window and of an ultrasonic probe) will now be described in more detail with reference to FIGS. 1 to 3. In these different figures, the equivalent elements are designated by the same reference number.

1. General Principle

The assembly for treating a brain tissue comprises:
An acoustic window 1, and
A probe 2 able to generate ultrasonic waves.

This assembly allows a practitioner to treat the brain tissue by using ultrasounds.

The window 1 is intended to be implanted into the patient, in particular at an opening arranged in his cranium 4. This provides a protection to the brain and prevents its deformation due to pressure changes. The window 1 is advantageously made of an acoustically transparent material—polymeric material (such as polyethylene, polystyrene, acrylic, polyetheretherketone (PEEK) or poly(methyl methacrylate) (PMMA)) or a thermoplastic elastomer (such as PEBAX)—to enable the passage of the ultrasonic waves generated by the probe 2 in order to treat a brain tissue.

The probe 2 is adapted to be handled by the practitioner, or by an automatic displacement system carrying the probe. It comprises a casing 23 in which transducers 21 are housed for the generation of ultrasonic waves. The transducers may be arranged in a linear or matrix array of phased array transducers. Such phased array transducers may be independently controlled to generate acoustic signals having different phases in order to vary the direction of propagation of the ultrasonic waves. The casing is connected to a control device via an electrically conductive cable 22.

The probe 2 is intended to be positioned in line with the window 1 in order to allow treating a target area. However, once implanted, it is difficult to determine the position of the acoustic window 1, the latter being covered by the skin of the patient's skull. It is also difficult to determine what fraction of the emitted acoustic waves will actually reach the target after the acoustic window and the proximal brain tissues have passed through the skin of the patient, especially if hair is present.

This is why the inventors have developed a method for controlling a probe for the treatment of a brain tissue from an assembly composed of an acoustic window and of the ultrasonic probe.

2. Control Method

An example of a control method will now be described with reference to FIG. 2.

Once the window is implanted (step 100), the method comprises two phases:
- A first detection phase 10 consisting of assisting the practitioner in positioning the ultrasonic probe 2 relative to the acoustic window 1,
- A second treatment phase 20 consisting of generating ultrasonic waves for treating a brain tissue.

During the detection phase, the control device controls the ultrasonic probe 2 to enable detection of the position of the transducers 21 relative to the acoustic window 1. For example, the control device controls the switching of the probe 2 in an operating mode called "A-mode ultrasonography" (also called "A-scan" or "A-mode"). The A-mode ultrasonography is based on the emission of acoustic information and the reception of echoes along a propagation line. Alternatively, the control device can control specific transceivers integrated to the probe 2 and associated with the different transducers 21.

During the treatment phase, the control device controls the ultrasonic probe 2 to enable the treatment of a brain tissue of interest. For example, the control device controls the switching of the probe 2 in an operating mode called "treatment" mode during which each activated transducer 21 emits therapeutic ultrasonic waves (focused or unfocused) of greater intensity.

2.1. Detection Phase

The detection phase makes it possible to determine whether the transducers of the probe are positioned:
- above the acoustic window 1 or
- above the cranium 4 of the patient.

This detection phase also makes it possible to determine whether the acoustic coupling between the probe and the target tissue is acceptable, in particular for the transducers detected as being situated above the acoustic window.

To determine whether the transducers of the probe are correctly positioned on the one hand, and to evaluate the quality of the acoustic coupling on the other hand, one solution may consist of using the technique called "ultrasonographic reflection" technique.

This "ultrasonographic reflection" technique can be based on the evaluation of the energy contained in the return echo. More specifically, if for a considered transducer:
- the energy contained in the return echo signal is very high (i.e. greater than a first energy threshold value called "maximum" value), then the considered transducer extends in line with the bone of the cranium;
- the energy contained in the return echo signal is very low (i.e. smaller than a second energy threshold value called "minimum" value), then the considered transducer extends in line with the acoustic window;
- the energy contained in the return echo signal is comprised between the minimum energy threshold value and the maximum energy threshold value, then the transducer extends in line with the window, but the acoustic coupling is of poor quality, for example due to air bubbles around the patient's hair.

Alternatively (or in combination), the "ultrasonographic reflection" technique may be based on the evaluation of a flight time of the return echo. More precisely if for a considered transducer:
- the duration between the emission of acoustic information and the reception of a return echo is smaller than a first time threshold value, then the acoustic coupling is of poor quality, for example due to air bubbles around the patient's hair;
- the duration between the emission of acoustic information and the reception of a return echo is smaller than a second time threshold value greater than the first time threshold value, then the acoustic coupling is of good quality but the considered transducer extends in line with the cranium bone;
- the duration between the emission of acoustic information and the reception of a return echo is greater than the second time threshold value (or than a third time threshold value greater than the first and second time threshold values), then the acoustic coupling is of good quality and the considered transducer extends in line with the acoustic window.

The detection phase 10 comprises a step of displacing 200 the ultrasonic probe 2. The casing 23 of the probe 2 is plated on the skin 3 of the cranium 4 of the patient, and then displaced. During the displacement of the casing 23, the control device emits control signals to the transducers 21 (or to the specific transceivers) to determine their position relative to the acoustic window 1. These control signals can be emitted periodically (every one millisecond or every one second as a function of the speed of displacement of the probe).

At each reception of a control signal, each transducer 21 (or specific transceiver) generates low intensity ultrasonic waves toward the skull 4 of the patient, and detects echoes emitted by reflection.

The echoes recorded by each transducer 21 (or specific transceiver) are transmitted to the control device via the cable 22.

For each transducer 21, the control device processes the recorded echoes in order to determine (step 300) whether the transducer (or specific transceiver) is positioned above:
- the acoustic window 1, or above,
- the cranium 4 of the patient.

This determination of the position of each transducer 21 (or specific transceiver) can be obtained by comparing each recorded echo with reference signals and/or by detecting a variation of the echo level and/or its appearance time (for example a decrease in its intensity or a delay in its appearance).

At each emission of a control signal, the control device is able to determine whether a transducer is situated above the acoustic window 1 or not, and therefore to calculate the number of transducers 21b situated above the acoustic window 1.

This number of transducers 21b is compared (step 400) with a threshold value to determine whether enough transducers are positioned above the acoustic window 1 to enable the treatment of the brain tissue. Of course, the threshold value may vary depending in particular on the desired treatment.

Figure 3A:
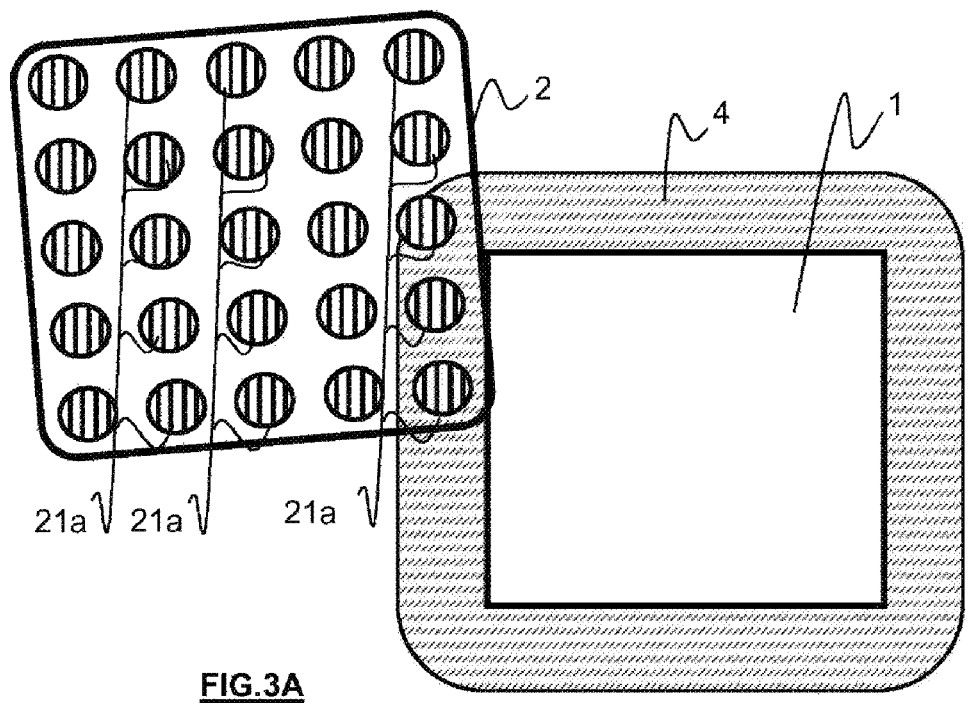
Figure 3B:
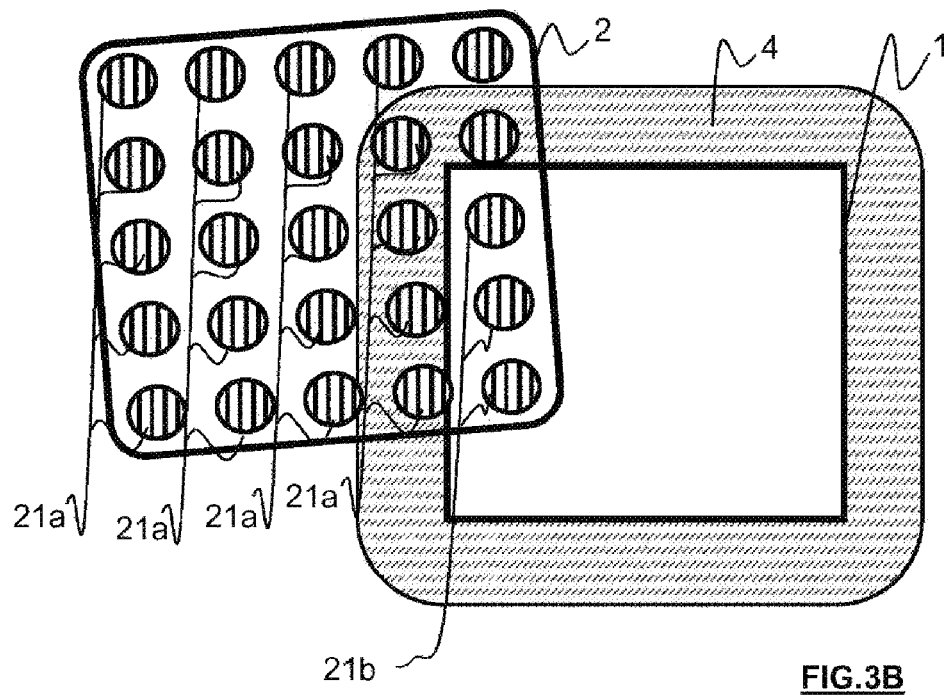

If the number of transducers 21b situated above the acoustic window 1 is less than the threshold value, then too few transducers are correctly positioned to ensure good effectiveness in the treatment. For example, FIG. 3A illustrates an example of positioning the probe 2 relative to the acoustic window 1 in which no transducer is positioned above the acoustic window 1. FIG. 3B illustrates an example of positioning the probe 2 in which only three transducers 21b extend above the acoustic window 1, the threshold value being for example equal to "9".

In these two cases, the number of transducers 21b situated in line with the acoustic window 1 is insufficient. The steps of displacing the casing 23 and determining the position of the transducers 21 are repeated until obtaining a sufficient number of transducers 21b positioned on the acoustic window 1.

Advantageously, the method may comprise a step of emitting information to the practitioner (or to the automatic displacement system carrying the probe) to show him a direction in which to displace the probe 2. This information may consist of a visual stimulus (displayed on means for displaying the control device) and/or sound stimulus (emitted on a loudspeaker of the control device) and/or tactile stimulus (by vibration of the casing 23 of the probe 2).

Figure 3C:
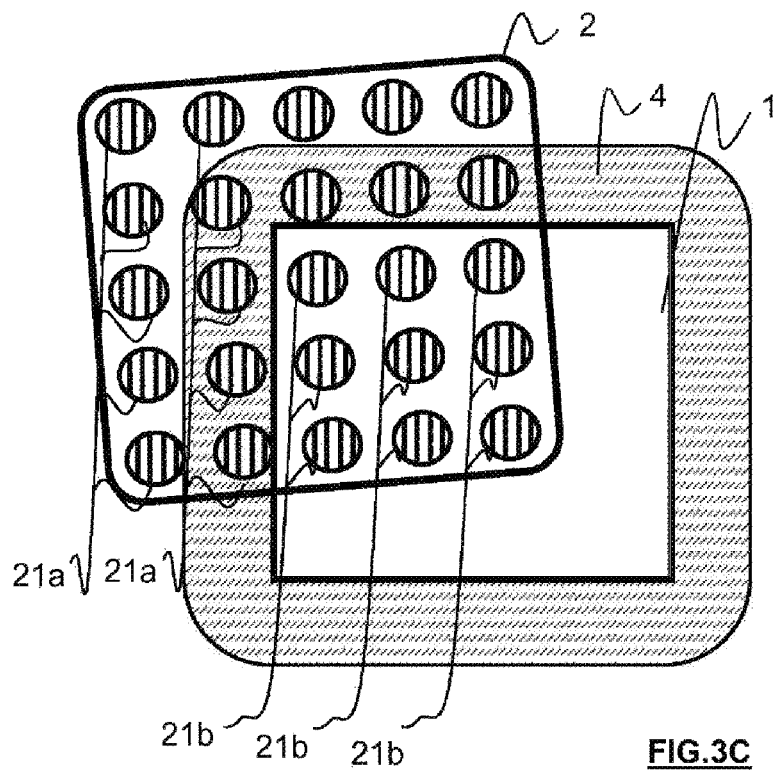
Figure 3D:
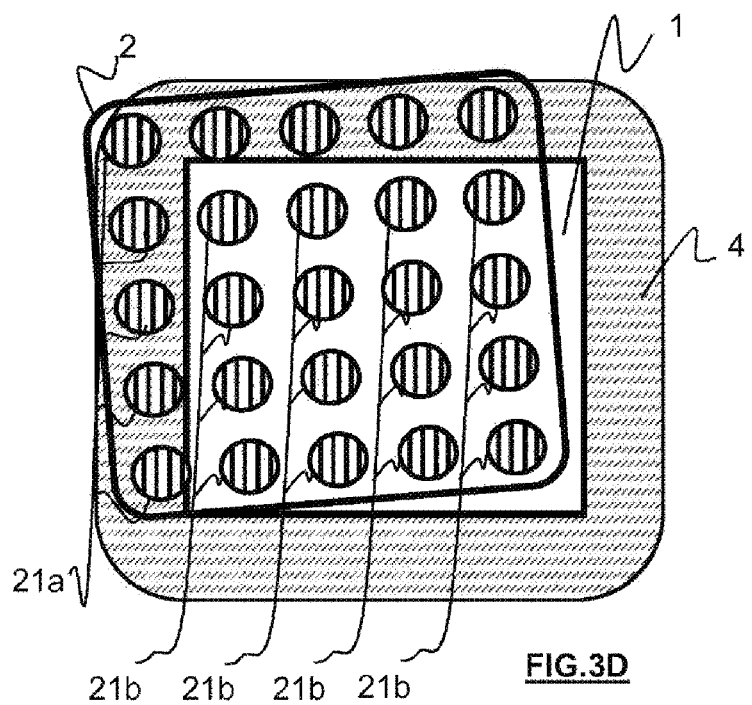

If the number of transducers 21b situated above the acoustic window 1 is greater than the threshold value, then enough transducers are correctly positioned to ensure good effectiveness of the treatment. For example, FIG. 3C illustrates an example of probe 2 positioning relative to the acoustic window 1 in which nine transducers 21b are positioned aims above the acoustic window 1, the threshold value being for example equal to "9". FIG. 3D illustrates an example of probe positioning in which sixteen transducers 21b extend above acoustic window 1, the threshold value being equal to "9".

In these two cases, the number of correctly positioned transducers 21b being sufficient, the following steps of the method can be implemented.

In one variant, the method may comprise a step of refocusing the probe above the acoustic window, even if the number of properly positioned transducers is sufficient. This step allows ensuring a repeatability of the treatment between two successive treatment sessions. The refocusing step comprises for example the sub-steps consisting of:
  comparing the position of the barycentre of all the probe transducers with the position of the barycentre of the probe transducers identified as being above the acoustic window,
  controlling the displacement of the probe if the distance between the barycentre of all the probe transducers and the barycentre of the probe transducers properly positioned above the acoustic window is greater than a predefined threshold value.

Advantageously, the control device can emit a visual and/or sound stimulus to warn the practitioner that it is no longer necessary to displace the probe 2. The practitioner then holds the probe 2 in position.

Once the probe is correctly positioned, the method may comprise a step of orienting the probe to emit the ultrasonic waves in a direction of interest. This direction of interest depends in particular on the size of the acoustic window and/or on the depth of the brain tissue to be treated. Indeed, the dimensions of the acoustic window may vary depending on the depth of the brain tissue (including a tumor) to be treated or imaged, a small-dimensioned window being preferable. For example, in the case of a deep tumor, the dimensions of the acoustic window may be smaller than the dimensions of the tumor, whereas in the case of a superficial tumor (i.e. close to the cranium), the dimensions of the window will be preferably equal to (or greater than) the dimensions of the tumor. Indeed, in the case of a deep tumor, it is possible to treat the entire tumor from an acoustic window (of smaller dimensions than the tumor) by varying the orientation of the probe.

Thus, the method may comprise a step of orienting the probe to emit the ultrasonic waves in one (or more) direction(s) of interest in order to treat the target brain tissue by emitting ultrasonic waves at different angles of incidence.

The control device then calculates 500 treatment parameters comprising in particular the intensity and the duration of emission of the ultrasonic waves to be generated by the transducers 21b situated above the acoustic window 1. Also, in the case where the probe comprises multidirectional phased-array transducers, the treatment parameters may comprise the direction of emission of the ultrasonic waves.

These treatment parameters are calculated as a function of the number of transducers 21b situated above the acoustic window 1.

For example, in the configuration illustrated in FIG. 3D, where sixteen transducers 21b are situated above the acoustic window 1, the calculated emission intensity and/or duration will be possibly smaller than the calculated intensity and/or duration in the configuration illustrated in FIG. 3C where only nine transducers 21b are positioned above the acoustic window 1.

2.2. Treatment Phase

Once the treatment parameters are calculated, the control device switches the probe 2 into the effective operating mode.

The transducers 21b situated above the acoustic window 1 are activated while the transducers 21a situated above the cranium 4 are deactivated.

In response to an input signal (i.e. an ultrasound generation signal), the activated transducers 21b can emit ultrasonic waves that pass through the acoustic window 1 and propagate up to the brain tissue to be treated. The deactivated transducers 21a, for their part, cannot emit ultrasonic waves in response to an input signal.

This allows avoiding the risks of burning of the patient.

During the treatment phase, several successive generations of ultrasonic waves by the activated transducers 21b can be implemented successively. Advantageously, a step of locating the position and orientation of the probe can be performed between each generation of ultrasonic waves by the activated transducers 21b. This makes it possible to guarantee the effectiveness of the treatment at each successive generation of ultrasonic waves by the activated transducers 21b.

Two examples of treatment performed from the method described above will now be presented.

2.3. First Example of Treatment

A first example of treatment comprises the following steps.

An acoustic window is implanted during the surgical resection performed for the ablation of the tumor. Thus, a separate surgery is not necessary later for the implantation of the acoustic window.

A succession of treatment sessions can then be provided to the patient to treat the pathology affecting him.

Before each new treatment session, the practitioner performs an MRI and uses a software tool to reveal the tumor and the improvement/infiltration region on the images T2.

A treatment is simulated with a software tool to plan the sonication, the appropriate phasing and the mechanical movement of the probe during the sonication.

The temperature on the surface of the window, the temperature of neighboring points on the surface of the skull as well as the quality of the acoustic coupling can be monitored, for example by measuring the acoustic power reflected toward the probe. This allows stopping the treatment if the temperature of the window and/or of the patient's skull surface exceeds a critical threshold value.

Micro-bubbles of contrast agents may be injected to the patient to improve the effectiveness of the ultrasonic wave treatment. Indeed, the oscillations of micro-bubbles of ultrasonic contrast agents under the action of ultrasounds generate a modulation of the permeability of the biological barriers of the cancer cells.

The ultrasonic waves are directed toward the brain tissue to be treated. The cavitation of the micro-bubbles is monitored. Each point of the brain tissue to be treated is subjected to ultrasonic waves according to a given "cavitation dose", or to a maximum amount of pulses (e.g. 100 pulses, etc.).

At each sonication point, the system compensates for the attenuation or reflection of the ultrasonic waves due to the acoustic window, to the brain tissues, and to the possible presence of an empty space of the tumor after resection. The quality of coupling and positioning of the probe can be controlled using positioning markers.

Advantageously, the step 500 of calculating the treatment parameters can take into account the lifetime of the contrast agent micro-bubbles (i.e. time difference between the injection of the micro-bubbles in the organism and their elimination at the pulmonary capillaries) in the determination of a duration for the treatment session.

Advantageously, the step 500 of calculating the treatment parameters can also take into account the signals called cavitation signals recorded by an ultrasonic sensor disposed in the probe in order to receive, through the window, the ultrasonic emissions emitted within the tissue.

2.4. Second Example of Treatment

A second example of treatment may comprise the following steps.

After implantation of the acoustic window, a magnetic resonance imaging (MRI pretreatment) can be implemented to segment:
the tumor area with respect to the acoustic window (for example in the case where MRI markers have been incorporated into the acoustic window), and
the acoustic window with respect to extracorporeal anatomical markers (for example ears, eyes, etc.) or implanted into the bone or the skin.

For the ultrasonic wave treatment, the practitioner can for example point these extracorporeal markers with the probe if the latter is associated with a neuro-navigation system. Such a system makes it possible to guide the practitioner in the positioning and orientation of the probe with respect to the acoustic window and with respect to the position of the brain tissue (tumor) to be treated. The association of the ultrasonic probe with a neuro-navigation system allows improving the spatial accuracy in the determination of the position and orientation of the probe.

The positioning of the probe and its coupling with the acoustic window can then be checked periodically (including during ultrasound treatment, to detect any movement of the patient, etc.) by using a specific "acoustic signature" from the acoustic window.

The reader will have understood that many modifications can be made to the invention described above without physically departing from the new teachings and advantages described here.

Accordingly, any modifications of this type are intended to be incorporated within the scope of the attached claims.

The invention claimed is:

1. A method for controlling a probe of an assembly for the treatment of a brain tumor, said assembly comprising the probe and an acoustic window made of an acoustically transparent material, and configured to be implanted at an opening arranged in the cranium of a patient, the probe including a plurality of ultrasonic wave generation transducers and being intended to be positioned in line with the acoustic window,
wherein the method comprises:
in a detection phase:
detecting which transducers of the probe are situated above the cranium of the patient,
detecting which transducers of the probe are situated above the acoustic window,
determining a barycentre of all probe transducers of the probe,
determining a barycentre of the transducers of the probe situated above the acoustic window,
determining a distance between the barycentre of all probe transducers and the barycentre of the transducers of the probe situated above the acoustic window, and
after determining that the distance between the barycentre of all probe transducers and the barycentre of the transducers of the probe situated above the acoustic window is greater than a predefined threshold value, causing the probe to be displaced,
wherein the detecting which transducers of the probe are situated above the cranium of the patient and which transducers are situated above the acoustic window comprises:
emitting, for each transducer, an ultrasonic measurement wave toward the patient's skull from the probe,
measuring, for each transducer, an ultrasonic echo wave reflected from the probe,
processing each ultrasonic echo wave to detect whether the associated transducer is situated above the acoustic window or above the cranium, and
processing each ultrasonic wave to estimate an acoustic coupling quality between the probe and the brain tumor; and
in a treatment phase:
deactivating the transducers of the probe situated above the cranium of the patient, and
activating the transducers of the probe situated above the acoustic window, said transducers being able to generate ultrasonic treatment waves in order to treat the brain tumor.

2. The control method according to claim 1, further comprising, in the detection phase, orienting the probe depending on the depth of the brain tumor to be treated.

3. The control method according to claim 1, further comprising, in the detection phase, calculating treatment parameters used during the treatment phase.

4. The control method according to claim 3, wherein the treatment parameters comprise the intensity and duration of emission of the ultrasonic waves to be generated by the transducers situated above the acoustic window.

5. The control method according to claim 3, wherein calculating the treatment parameters comprises at least one of the following:
calculating at least one treatment parameter as a function of the number of transducers situated above the acoustic window,
calculating at least one treatment parameter as a function of an attenuation or reflection coefficient associated with the acoustic window or with the tissues situated between the probe and the window, and/or of an attenuation coefficient associated with the material constituting a brain tissue traversed by the ultrasonic waves.

6. The control method according to claim 1, wherein processing each ultrasonic echo wave to detect whether the associated transducer is situated above the acoustic window or above the cranium comprises the comparison of the ultrasonic echo wave with reference signals, and the detection of a variation of an intensity of the ultrasonic echo wave and/or a variation in its appearance time.

7. The control method according to claim 1,
wherein causing the probe to be displaced comprises sending an instruction to displace the probe on the skull of the patient.

8. The control method according to claim 1, further comprising, in the detection phase, emitting displacement information, said displacement information indicating to the practitioner a direction of displacement of the probe.

9. The control method according to claim 1, wherein during the detection phase, the control device controls the probe by switching said probe in an A-mode ultrasonography in order to enable detection of the position of the transducers relative to the acoustic window.

10. A non-transitory computer readable medium storing a program with code instructions for applying a method for controlling a probe of an assembly for the treatment of a brain tumor when said program is run on a computer, the assembly comprising the probe and an acoustic window made of an acoustically transparent material and configured to be implanted at an opening arranged in the cranium of a patient, the probe including a plurality of ultrasonic wave generation transducers and being intended to be positioned in line with the acoustic window, wherein the method comprises:
in a detection phase:
detecting which transducers of the probe are situated above the cranium of the patient,
detecting which transducers of the probe are situated above the acoustic window,
determining a barycentre of all probe transducers of the probe,
determining a barycentre of the transducers of the probe situated above the acoustic window,
determining a distance between the barycentre of all probe transducers and the barycentre of the transducers of the probe situated above the acoustic window, and
after determining that the distance between the barycentre of all probe transducers and the barycentre of the transducers of the probe situated above the acoustic window is greater than a predefined threshold value, causing the probe to be displaced,
wherein detecting which transducers of the probe are situated above the cranium of the patient and which transducers are situated above the acoustic window comprises:
emitting, for each transducer, an ultrasonic measurement wave toward the patient's skull from the probe,
measuring, for each transducer, an ultrasonic echo wave reflected from the probe,
processing each ultrasonic echo wave to detect whether the associated transducer is situated above the acoustic window or above the cranium, and
processing each ultrasonic wave to estimate an acoustic coupling quality between the probe and the brain tumor; and
in a treatment phase:
deactivating the transducers of the probe situated above the cranium of the patient, and
activating the transducers of the probe situated above the acoustic window, said transducers being able to generate ultrasonic treatment waves in order to treat the brain tumor.

11. The non-transitory computer readable medium of claim 10, wherein the method further comprises orienting the probe based on the depth of the brain tumor to be treated.

12. The non-transitory computer readable medium of claim 10, wherein the method further comprises calculating treatment parameters used during the treatment phase.

13. The non-transitory computer readable medium of claim 10, wherein processing each ultrasonic echo wave to detect whether the associated transducer is situated above the acoustic window or above the cranium comprises:
comparing the ultrasonic echo wave with reference signals, and the
detecting a variation of an intensity of the ultrasonic echo wave or an appearance time of the ultrasonic echo wave.

14. The non-transitory computer readable medium of claim 10, wherein the method further comprises emitting displacement information indicating a direction of displacement of the probe.

15. A device for treating a brain tumor comprising an acoustic window made of an acoustically transparent material and configured to be implanted at an opening arranged in the cranium of a patient, and a probe including a plurality of ultrasonic waves generation transducers, the probe being intended to be positioned in line with the acoustic window, wherein the device comprises a control device for implementing a method for controlling the probe, wherein the method comprises:
in a detection phase:
detecting which transducers of the probe are situated above the cranium of the patient,
detecting which transducers of the probe are situated above the acoustic window,
determining a barycentre of all probe transducers of the probe,
determining a barycentre of the transducers of the probe situated above the acoustic window,
determining a distance between the barycentre of all probe transducers and the barycentre of the transducers of the probe situated above the acoustic window, and
after determining that the distance between the barycentre of all probe transducers and the barycentre of the transducers of the probe situated above the acoustic window is greater than a predefined threshold value, causing the probe to be displaced, wherein the detecting which transducers of the probe are situated above the cranium of the patient and which transducers are situated above the acoustic window comprises:

emitting, for each transducer, an ultrasonic measurement wave toward the patient's skull from the probe, measuring, for each transducer, an ultrasonic echo wave reflected from the probe, processing each ultrasonic echo wave to detect whether the associated transducer is situated above the acoustic window or above the cranium, and processing each ultrasonic wave to estimate an acoustic coupling quality between the probe and the brain tumor; and in a treatment phase:

deactivating the transducers of the probe situated above the cranium of the patient, and activating the transducers of the probe situated above the acoustic window, said transducers being able to generate ultrasonic treatment waves in order to treat the brain tumor.

16. The device of claim 15, wherein the method further comprises orienting the probe based on the depth of the brain tumor to be treated.

17. The device of claim 15, wherein the method further comprises calculating treatment parameters used during the treatment phase.

18. The device of claim 15, wherein processing each ultrasonic echo wave to detect whether the associated transducer is situated above the acoustic window or above the cranium comprises:

comparing the ultrasonic echo wave with reference signals, and the detecting a variation of an intensity of the ultrasonic echo wave or an appearance time of the ultrasonic echo wave.

19. The device of claim 15, wherein the method further comprises emitting displacement information indicating a direction of displacement of the probe.

* * * * *